US009255301B2

(12) United States Patent
Sanders et al.

(10) Patent No.: US 9,255,301 B2

(45) Date of Patent: Feb. 9, 2016

(54) PROCESS FOR THE CRYSTALLISATION OF A WATER-SOLUBLE COMPOUND

(75) Inventors: Johan Pieter Marinus Sanders, Groningen (NL); Marieke Elisabeth Bruins, Wageningen (NL); Jeroen Johannes Cornelis Franciscus Van Bon, Bemmel (NL)

(73) Assignee: Wageningen Universiteit, Wageningen (NL)

( * ) Notice: Subject to any disclaimer, the term of this patent is extended or adjusted under 35 U.S.C. 154(b) by 37 days.

(21) Appl. No.: 14/006,459

(22) PCT Filed: Mar. 19, 2012

(86) PCT No.: PCT/NL2012/050169

§ 371 (c)(1), (2), (4) Date: Nov. 25, 2013

(87) PCT Pub. No.: WO2012/128624

PCT Pub. Date: Sep. 27, 2012

(65) Prior Publication Data

US 2014/0087437 A1 Mar. 27, 2014

(30) Foreign Application Priority Data

Mar. 22, 2011 (NL) ..................................... 2006447

(51) Int. Cl.

| | |
|---|---|
| ***C13B 30/02*** | (2011.01) |
| ***C12P 5/02*** | (2006.01) |
| ***C12P 7/06*** | (2006.01) |
| ***C12P 7/16*** | (2006.01) |
| ***B01D 9/00*** | (2006.01) |

(52) U.S. Cl.

CPC ............ *C13B 30/021* (2013.01); *B01D 9/0054* (2013.01); *C12P 5/023* (2013.01); *C12P 7/06* (2013.01); *C12P 7/16* (2013.01); *C13B 30/022* (2013.01); *Y02E 50/17* (2013.01); *Y02E 50/343* (2013.01)

(58) Field of Classification Search

None

See application file for complete search history.

(56) References Cited

FOREIGN PATENT DOCUMENTS

| | | | |
|---|---|---|---|
| EP | 0 156 596 | A2 | 10/1985 |
| GB | 1 268 563 | | 3/1972 |
| WO | WO-03/016577 | A1 | 2/2003 |
| WO | WO-2009/049391 | A1 | 4/2009 |

OTHER PUBLICATIONS

Hunter, Allen Hunter's Youngstown State University X-Ray Structure Analysis Lab Manual: Chapter XIV: Growing Single Crystals, Mar. 13, 2000.*

Gyorgydeak, Monosaccharide Sugars: Chemical Synthesis by Chain Elongation, Degradation, and Epimerization, Academic Press, Jan. 22, 1998, p. 21.*

Sigma-Aldrich, Molecular Sieves, Technical Information Bulletin, Feb. 25, 2010.*

UMSL, internet article, www.umsl.edu/~orglab/pdffiles/practice.pdf, published Nov. 2009 as found in web.archive.org.*

International Search Report mailed May 14, 2012 in International Appln No. PCT/NL2012/050169, including Written Opinion.

* cited by examiner

*Primary Examiner* — Layla Bland

(74) *Attorney, Agent, or Firm* — Foley & Lardner LLP; Sunit Talapatra

(57) ABSTRACT

A process for the crystallization of a water-soluble compound from a solution of water and a solvent is provided. A process for the manufacture of crystalline sucrose from sugar palm juice or sucrose-containing biomass comprising such crystallization process is also disclosed.

27 Claims, 1 Drawing Sheet

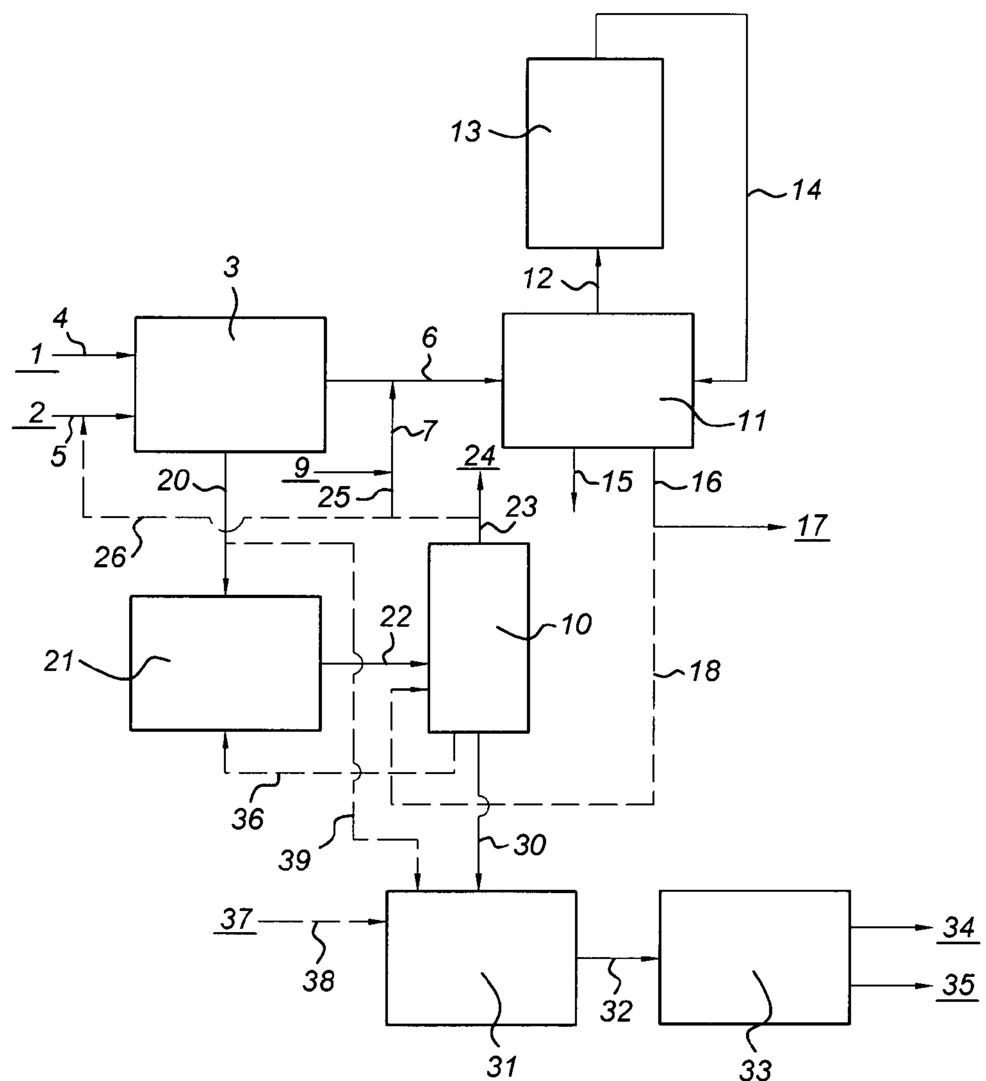
1
2
3
4
5
6
7
9
10
11
12
13
14
15
16
17
18
20
21
22
23
24
25
26
30
31
32
33
34
35
36
37
38
39

PROCESS FOR THE CRYSTALLISATION OF A WATER-SOLUBLE COMPOUND

CROSS-REFERENCE TO RELATED APPLICATIONS

This application is the National Phase of International Patent Application No. PCT/NL2012/050169, filed Mar. 19, 2012, published as WO 2012/128624, which claims priority to Netherland Application No. 2006447, filed Mar. 22, 2011. The contents of this application is herein incorporated by reference in its entirety.

FIELD OF THE INVENTION

The present invention relates to a process for the crystallisation of a water-soluble compound from a solution and to a process for the manufacture of crystalline sucrose from sugar palm juice or sucrose-containing biomass, which process comprises such crystallisation process.

BACKGROUND OF THE INVENTION

Processes for the crystallisation of water-soluble compounds from an aqueous solution are energy and capital intensive. An example of a process wherein such crystallisation plays an important role is the process for producing crystalline sucrose from sucrose-containing biomass, such as for example sugar beets including tropical beet, and sugar cane and from sugar palm juice.

In the conventional process for the manufacture of crystalline sucrose from sugar beets, the sucrose is extracted from comminuted beet strips with water in an extractor that is commonly called a diffuser. The sucrose-containing liquid that exits the diffuser is known as raw juice and is subjected to a carbonatation process in order to remove impurities that could frustrate the crystallisation process. Examples of such impurities are multivalent anions (e.g. sulphate, phosphate, citrate and oxalate), proteins, amino acids, saponins, pectins and monosaccharides such as glucose and fructose. The so-called thin juice that is obtained after carbonatation is evaporated to obtain a thick juice with a sucrose content of approximately 60%. The thick juice is fed to a crystalliser where it is seeded with fine sucrose crystals and further concentrated under vacuum to form crystallised sucrose. Liquid is removed from the sucrose crystals formed by centrifugation.

The conventional process is optimised towards the yield of crystalline sucrose from the biomass.

Disadvantages of the conventional process are that the process is highly energy and capital intensive and that costs to transport the voluminous beets to the sucrose production site are high. Moreover, the conventional process is directed towards optimization of the yield of crystalline sucrose, a product that is currently facing lower selling prices.

SUMMARY OF THE INVENTION

It has now been found that water-soluble compounds can be crystallised in a process that is less energy-intensive by using a crystallisation step, wherein, in a crystallisation vessel, a solution of the water-soluble compound in a mixture of water and a solvent that is miscible with water is provided. The solvent is chosen such that the solubility of the water-soluble compound is lower in the solvent than in water. The solvent concentration in the mixture is subsequently increased in order to allow the water-soluble compound to crystallise and precipitate in the liquid mixture. The solvent concentration is increased by passing vapour phase of the water-solvent mixture over a sorbent that selectively adsorbs water to obtain a vapour phase depleted in water and enriched in solvent and either recycling at least part of the vapour phase depleted in water to the crystallisation vessel or by withdrawing such vapour phase from the process and adding solvent from an external source to the crystallisation vessel.

Accordingly, the present invention relates to a process for the crystallisation of a water-soluble compound from a solution comprising the following steps:

a) providing, in a crystallisation vessel, a solution of the water-soluble compound in a mixture of water and a solvent in which the water-soluble compound has a lower solubility than in water;

b) passing vapour phase of the mixture through a sorption zone containing a water vapour sorbent to selectively adsorb water from the vapour phase to obtain a vapour phase depleted in water and enriched in the solvent and water-saturated water vapour sorbent;

c) enriching the mixture in the crystallisation vessel in solvent by recycling at least part of the vapour phase depleted in water and enriched in the solvent to the crystallisation vessel or withdrawing vapour phase depleted in water from the process and adding solvent from an external source to the crystallisation vessel;

d) allowing solid crystals of the water-soluble compound to precipitate from the solution in the crystallisation vessel at a crystallisation temperature; and e) discharging precipitated solid crystals of the water-soluble compound from the crystallisation vessel and discharging a solution of non-crystallised water-soluble compound in water-solvent mixture from the crystallisation vessel.

The crystallisation process according to the invention is particularly suitable to be used in a process for the manufacture of sucrose from sugar palm juice or from sucrose-containing biomass, wherein the water-soluble solvent is an alcohol having one to four carbon atoms.

Accordingly, the invention further relates to the manufacture of crystalline sucrose from sugar palm juice comprising the crystallisation process as defined hereinabove, wherein the solution of sucrose in the mixture of water and alcohol in the crystallisation vessel is provided (step a) by diluting sugar palm juice with the alcohol or with water and the alcohol and supplying the diluted juice to the crystallisation vessel.

In a still further aspect, the invention relates to a process for the manufacture of crystalline sucrose from sucrose-containing biomass comprising the crystallisation process as defined hereinabove, wherein the solution of sucrose in the mixture of water and alcohol in the crystallisation vessel is provided (step a) by:

a1) extracting comminuted sucrose-containing biomass with an aqueous liquid selected from water or a mixture of water and the alcohol to obtain a solution of sucrose in the aqueous liquid and solid extracted biomass comprising remaining sucrose;

a2) separating the solution of sucrose from the solid extracted biomass; and a3) supplying the solution to the crystallisation vessel or, in case the aqueous liquid is water, supplying both the solution and a stream of the alcohol to the crystallisation vessel.

An advantage of the process for the manufacture of crystalline sucrose according to the invention is that the alcohol is a so-called antisolvent for sucrose and thus promotes crystallisation of the sucrose. Other advantages are that the solvent acts as anti-foaming agent and as disinfectant in the crystallisation vessel. Another advantage of the presence of the alcohol during the sucrose crystallisation step and of the presence of a solvent in the crystallisation step of any water-soluble compound including sucrose, is that the viscosity of the mixture in the crystallisation vessel remains sufficiently low, also at a relatively high concentration of the water-soluble compound. Further, impurities, such as compounds resulting in undesired colouring, will be partly extracted into the solvent.

If in the crystallisation process according to the invention ethanol or 1-butanol is used as solvent, the process is particularly suitable to be used in a process for the manufacture of both crystalline sucrose and ethanol or 1-butanol from sucrose-containing biomass or sugar palm juice. In such process, ethanol or 1-butanol is produced by fermentation of remaining, non-crystallised sucrose and/or of other organic compounds in the biomass. Part of the alcohol produced by such fermentation can advantageously be used as the solvent.

Further advantages can be obtained in the process for the manufacture of crystalline sucrose from sucrose-containing biomass according to the invention if waste of the biomass, i.e. from the sugar palm or from the biomass to be extracted, such as leaves and small particles and/or waste streams from the ethanol or 1-butanol fermentation step are anaerobically fermented to produce biogas. The biogas on its turn can be used to fuel an engine to produce energy and heat. The heat thus-produced can suitably be used to regenerate the saturated water vapour sorbent. Even further integration advantages are obtained by using steam obtained in the regeneration of the water vapour sorbent to strip or distill the alcohol from the fermentation broth and/or to heat the crystallisation vessel to the crystallisation temperature.

Thus, the invention provides a highly integrated process which is far less capital and energy intensive than the conventional process for manufacturing sucrose from sucrose-containing biomass. Due to the decreased capital and energy intensity, the process is particularly suitable to be carried out on a smaller scale and can thus be carried out at a location close to fields where the sugar crops are harvested, resulting in lower transportation costs.

The yield of crystalline sucrose obtained in the process according to the invention is lower than the yield of crystalline sucrose in the conventional process for the manufacture of sucrose from sugar beets. This disadvantage is, however, far outweighed by the above-mentioned advantages of the process, certainly in view of the tendency of lower guaranteed minimum prices for crystalline sugar by the European Union. Moreover, there are attractive outlets for other products that may be produced by the process according to the invention, such as ethanol or 1-butanol, streams comprising non-crystallised sucrose or other organic compounds and biogas.

SUMMARY OF THE DRAWING

In the FIGURE is schematically shown a process for producing sucrose and ethanol from sugar beet according to the invention.

DETAILED DESCRIPTION OF THE INVENTION

In the crystallisation process according to the invention, a solution of a water-soluble compound in a mixture of water and a solvent in which the water-soluble compound has a lower solubility than in water, is provided in a crystallisation vessel.

The water-soluble compound may be any water-soluble compound that may form crystals. Examples of suitable water-soluble compounds are saccharides having up to five monose units. Saccharides having one or two monose units, for example glucose, lactose or sucrose, are preferred water-soluble compounds. Sucrose is a particularly preferred water-soluble compound.

The solvent may be any solvent that can form a mixture with water, i.e. a solvent that is miscible with water under the conditions prevailing in the crystallisation vessel, and in which the water-soluble compound to be crystallised has a lower solubility than in water. Suitable solvents include water-miscible alcohols with one to four carbon atoms, such as methanol, ethanol, 1-propanol, 2-propanol, 1-butanol, 2-butanol, isobutanol, or tert-butanol, mixtures of two or more of such alcohols, acetonitrile and pyridine. It will be appreciated that it depends inter alia on the compound to be crystallised which solvent can be suitably used. Preferably, the solvent is an alcohol with one to four carbon atoms or a mixture of two or more of such alcohols, more preferably the solvent is ethanol or 1-butanol. The solvent may comprise a single compound or may be a mixture of compounds. In case the solvent is a mixture of compounds, the water-soluble compound to be crystallised has a lower solubility in the solvent as a whole, i.e. in the mixture of compounds, than in water.

The solvent preferably has a boiling point or boiling range that is close to the boiling point of water in order to allow a vapour phase comprising both water and solvent to be formed for passing through the water vapour sorption zone in step b). The boiling point is preferably within 50° C. from the boiling point of water, more preferably within 40° C., even more preferably within 25° C.

In the case of sucrose as water-soluble compound, the solvent is preferably an alcohol that may be manufactured from fermentation of the sucrose itself or from the biomass from which the sucrose is extracted. Examples of such alcohols are ethanol and 1-butanol. Ethanol is a particularly preferred solvent in case the water-soluble compound to be crystallised is sucrose.

The mixture in the crystallisation vessel is kept at a crystallisation temperature. The crystallisation temperature is such temperature that a vapour phase of the mixture is formed above the liquid phase of the mixture. At least part of the vapour phase is passed through a sorption zone containing a water vapour sorbent to selectively adsorb water from the vapour phase. In this way, a vapour phase depleted in water and enriched in the solvent is obtained and the water vapour sorbent becomes saturated with water. The water-saturated water vapour sorbent thus obtained may be regenerated by techniques known in the art. Preferably, the water-saturated water vapour sorbent is regenerated by heating the sorbent, typically to a temperature in the range of from 130 to 400° C.

In step c) of the process, the water-solvent mixture in the crystallisation vessel is enriched in solvent, typically by recycling at least part of the vapour phase depleted in water that is formed in the sorption zone in step b) to the crystallisation vessel. Alternatively, vapour phase obtained in step b) is withdrawn from the process and solvent from an external source is added to the crystallisation vessel in order to increase the solvent concentration in the mixture in the crystallisation vessel. A combination of recycling of solvent-enriched vapor phase and addition of external solvent may be applied in step c). By increasing the solvent concentration and lowering the water concentration in the crystallisation vessel, solid crystals of the water-soluble compound will be allowed to precipitate at the crystallisation temperature.

The recycling may be done in any suitable way, preferably by bubbling vapour phase through the liquid mixture in the crystallisation vessel. An advantage of recycling of solvent is that the heat of condensation produced in the sorption zone is retained in the process an no or less heating of the crystallisation vessel is needed in order to maintain the crystallisation temperature.

The crystallisation temperature may be any temperature at which water-soluble compound can crystallise in the mixture and at which sufficient water is evaporated. In order to avoid thermal degradation of the water-soluble compound, the crystallisation temperature is preferably below 150° C., more preferably below 120° C., even more preferably below 105° C. In order to allow for sufficient water vapour absorption, the crystallisation temperature is preferably above 20° C., more preferably above 50° C. A crystallisation temperature in the range of from 60 to 90° C. is particularly preferred. It will be appreciated that the crystallisation temperature will be at most the boiling temperature of the solution at the pressure prevailing in the crystallisation vessel. The crystallisation may be carried out at any suitable pressure, preferably at approximately atmospheric pressure.

After precipitation, the solid crystals of the water-soluble compound are discharged from the crystallisation vessel. This may be done continuously or batchwise. A solution of non-crystallised water-soluble compound in water-solvent mixture is discharged from the crystallisation vessel. This may be done continuously or batchwise. The solution of non-crystallised water-soluble compound may be subjected to a further crystallisation step which may be a crystallisation step according to the invention (step a) to d)) or a different crystallisation step.

The crystallisation process according to the invention, i.e. the whole of steps a) to d), may be carried out batch-wise, semi-continuously or continuously.

Any water to solvent ratio may be used in the mixture that is provided to the crystallisation vessel in step a). It will be appreciated that the higher the solvent concentration in the mixture provided, the lower the decrease in water concentration needed to allow crystallisation of the water-soluble compound to take place. Preferably, a mixture is provided in step a) that has at least 10 vol % of solvent based on the total volume of water and solvent, more preferably at least 20 vol % of solvent. The solvent concentration in the mixture provided in step a) preferably does not exceed 50 vol %.

The water vapour sorbent may be any water vapour sorbent that is capable of selectively absorbing water vapour from the vapour phase of the mixture of water and solvent at the crystallisation temperature. Reference herein to selectively adsorbing water is to adsorbing water and solvent in a water to solvent ratio that is higher than the water to solvent ratio in the vapour phase that is passed through the sorption zone. Preferably, no substantial amount of solvent is adsorbed, i.e. less than 1% of the solvent passed through the sorption zone.

Typically, the water vapour sorbent is a molecular sieve. Any molecular sieve known to be a strong water vapour sorbent at the relatively low crystallisation temperature may be suitably used. Suitable molecular sieves include zeolites. Molecular sieves having pores that are sufficiently large to adsorb water but which are too small to adsorb the solvent are particularly preferred. Preferred sorbents are molecular sieves with pores having a minimum diameter in the range of from 2.8 to 4.0 Å, more preferably in the range of from 3.0 to 3.5 Å, most preferably about 3.0 Å. In the case of zeolites, the capability to adsorb molecules is determined by the dimensions of the channels in the zeolite, in particular the smallest diameter of the channels. Zeochem® molecular sieve Z3-03 is a commercially available molecular sieve that can be suitably used in the process according to the invention, in particular in case ethanol is used as solvent.

The crystallisation process according to the invention using an alcohol with one to four carbon atoms as solvent can be advantageously applied in a process for the manufacture of crystalline sucrose from sucrose-containing biomass such as sugar beet or sugar cane, or from sugar palm juice. In such process, a solution of sucrose in a mixture of water and the alcohol is provided in the crystallisation vessel (step a)).

In the process according to the invention for the manufacture of crystalline sucrose from sugar palm juice, the solution of sucrose in the mixture of water and alcohol in the crystallisation vessel is provided by diluting sugar palm juice with the alcohol or with a mixture of water and the alcohol and supplying the diluted juice to the crystallisation vessel. Sugar palm juice is typically obtained by directly tapping such juice from sugar palm trees.

In the process according to the invention for the manufacture of crystalline sucrose from sucrose-containing biomass, the solution of sucrose in the mixture is provided by first extracting comminuted sucrose-containing biomass with an aqueous liquid that may be either water or a mixture of water and the alcohol. Thus, a solution of sucrose in the aqueous liquid and solid extracted biomass still comprising remaining sucrose are obtained.

After extraction, the solution of sucrose and the solid extracted biomass are separated and the solution is supplied to the crystallisation vessel. If only water was used as extractant, also a stream of the alcohol will supplied to the crystallisation vessel, either by supplying it directly to the crystallisation vessel or by adding it to the solution prior to supplying it to the crystallisation vessel. In case a water-alcohol mixture was used, there may be no need to add further alcohol to the solution.

The actual crystallisation (steps b) to d)) will be carried out as described hereinabove, both in the process starting with sucrose-containing biomass and in the process starting with sugar palm juice.

Preferably, the process for the manufacture of crystalline sucrose from sucrose-containing biomass is a process for manufacturing both crystalline sucrose and ethanol or 1-butanol from that biomass. In such process, at least part of the remaining sucrose in the solid extracted biomass and/or of the non-crystallised sucrose in the solution that is discharged from the crystallisation vessel in step e) is fermented into ethanol or 1-butanol to obtain a fermentation broth comprising ethanol or 1-butanol (step f)). Fermentation techniques for fermenting sucrose into ethanol or 1-butanol are well-known in the art. Any suitable technique known in the art may be used. Typically ethanol fermentation will be a carried out by using yeasts and 1-butanol fermentation by using Clostridium species.

After or during fermentation, the alcohol produced will be separated from the fermentation broth to obtain alcohol product (step g)). Such separation may be carried out by any suitable techniques known in the art, preferably by stripping or by distillation. The alcohol product may be end product. Preferably, at least part of the alcohol produced in step f) is recycled to extraction step a1) or to the crystallisation vessel (step h)). Thus, no or a minimum amount of alcohol from an external source is needed.

Preferably, the process for the manufacture of crystalline sucrose according to the invention is further integrated by anaerobically fermenting organic compounds still present in waste streams of the process to produce biogas. Accordingly, the fermentation broth from which alcohol has been separated in step g) and/or the solid extracted biomass are, optionally together with leaves and/or small particles of the sucrose-containing biomass, anaerobically fermented to obtain biogas (step i)). The biogas is fuelling an engine to produce energy and heat (step (j)). The energy thus-produced may be advantageously used in the process itself or for a different purpose. The heat produced can suitably be used for the regeneration of the saturated water vapour sorbent.

Accordingly, the process preferably further comprises desorbing water from the saturated water vapour sorbent obtained in step b) by heating the saturated water vapour sorbent using the heat produced in step j) to obtain regenerated water vapour sorbent and steam (step k)).

The steam may be used for any purpose. Preferably, the steam obtained in step k) is used in the process itself, more preferably to separate the alcohol from the fermentation broth in step g) by means of stripping or distillation and/or to heat the crystallisation vessel to the crystallisation temperature.

DETAILED DESCRIPTION OF THE DRAWINGS

In the FIGURE is shown a process for the manufacture of crystalline sucrose and ethanol from sugar beet. Strips of sugar beet 1 and water 2 are supplied to extraction zone 3 via lines 4 and 5, respectively. In zone 3, sucrose is extracted from the strips, typically at a temperature in the range of from 40 to 90° C. A solution of sucrose is discharged from zone 3 via line 6. Ethanol is added to the sucrose solution via line 7, thus forming a sucrose solution in a water-ethanol mixture. The ethanol may be ethanol 9 from an external source or ethanol recycled from distillation unit 10. The sucrose solution in water-ethanol is supplied to crystallisation vessel 11. The solution in crystallisation vessel 11 is kept at a crystallisation temperature in the range of from 60 to 90° C. A vapour phase of the water-ethanol mixture is thus formed and pumped via line 12 to sorption zone 13. Sorption zone 13 contains a molecular sieve that selectively adsorbs water. A vapour phase enriched in ethanol is discharged from sorption zone 13 via line 14 and recycled to crystallisation vessel 11. Due to the decreased water content and increased ethanol concentration in the solution in vessel 11, sucrose is allowed to crystallise and precipitate. Precipitated solid crystals of sucrose 15 are discharged from crystallisation vessel 11. A solution comprising non-crystallised sucrose is discharged from vessel 11 via line 16. This solution may be discharged from the process via line 17. The solution discharged may for example be subjected to a second crystallization step (not shown). Optionally, all or part of the non-crystallised sucrose is supplied to distillation unit 10 via line 18 to separate the ethanol from the non-crystallised sucrose.

The extracted strips of sugar beet are discharged from extraction zone 3 via conduit 20 and supplied to fermentation reactor 21 wherein the remaining sucrose are fermented into ethanol. The fermentation broth thus obtained is supplied to distillation unit 10 via line 22, wherein ethanol is separated from the remaining biomass and water. Ethanol is discharged from distillation unit 10 via line 23 and withdrawn from the process as ethanol product 24 and/or added to the sucrose solution that is supplied to crystallisation vessel 11 via line 25 or to the water supplied to extraction zone 3 via line 26.

The biomass and water from which the ethanol is distilled is discharged from distillation unit 10 via line 30 and supplied to anaerobic fermentation reactor 31. In fermentation reactor 31, biogas is produced. The biogas is supplied via line 32 to engine 33. The biogas serves as fuel for engine 33 to produce energy 34 and heat 35. The heat 35 may be used to regenerate the saturated sorbent formed in sorption zone 13 (regeneration step not shown).

The non-crystallised sucrose from which ethanol is distilled in unit 10 may then be supplied to fermentation reactor 21 via line 36 or to fermentation reactor 31 to produce ethanol or biogas from the non-crystallised sucrose.

Optionally, biogas may be produced from waste biomass 37 from the sugar beets such as leaves and/or small particles and/or from extracted biomass from extraction zone 3 by supplying these streams to fermentation reactor 31 via lines 38 and 39, respectively.

EXAMPLES

The invention will be further illustrating in a non-limiting way by the following example.

Example

A solution of sucrose in a mixture of water and ethanol was provided to a crystallisation vessel. The solution contained 1 part sucrose on 4 parts water and 4 parts of ethanol (all on weight basis). During 16 hours, the solution was kept at 70° C. in the vessel and the vapour phase thus-formed was passed through a sorption column containing Zeochem Z3-03 molecular sieve. The temperature in the sorption column was 85° C. Vapour phase that had passed the sorption column and which was enriched in ethanol compared to the vapour phase entering the column, was continuously recycled to the crystallisation vessel by bubbling it through the liquid mixture in the vessel. After 16 hours, it was observed that the sucrose concentration in the mixture was increased and crystals of sucrose had precipitated from the mixture.

The invention claimed is:

1. A process for crystallisation of sucrose from a solution, comprising:

(a) providing, in a crystallisation vessel, a solution of the sucrose in a mixture of water and a solvent, wherein the sucrose has a lower solubility in the solvent than in water;

(b) passing vapour phase of the mixture through a sorption zone containing a water vapour sorbent to selectively adsorb water from the vapour phase to obtain a vapour phase depleted in water and enriched in the solvent and water-saturated water vapour sorbent;

(c) enriching the mixture in the crystallisation vessel in solvent by (i) recycling at least part of the vapour phase depleted in water and enriched in the solvent to the crystallisation vessel or (ii) withdrawing vapour phase depleted in water from the process and adding solvent from an external source to the crystallisation vessel;

(d) allowing solid crystals of the sucrose to precipitate from the solution in the crystallisation vessel at a crystallisation temperature; and (e) discharging precipitated solid crystals of the sucrose from the crystallisation vessel and discharging a solution of non-crystallised sucrose in water-solvent mixture from the crystallisation vessel.

2. The process according to claim 1, wherein the solvent is an alcohol with one to four carbon atoms or a mixture of two or more thereof.

3. The process according to claim 1, wherein the solvent is ethanol or 1-butanol.

4. The process according to claim 3, wherein the solvent is ethanol.

5. The process according to claim 2, wherein the sucrose is supplied to the crystallization vessel by diluting sugar palm juice with the alcohol or with water and the alcohol.

6. A process for the manufacture of crystalline sucrose from sucrose-containing biomass, comprising:

(a1) extracting comminuted sucrose-containing biomass with an aqueous liquid selected from water or a mixture of water and an alcohol with one to four carbon atoms or a mixture of two or more thereof, to obtain a solution of sucrose in the aqueous liquid and solid extracted biomass comprising remaining sucrose;

(a2) separating the solution of sucrose from the solid extracted biomass; and (a3) supplying the solution to a crystallisation vessel or, in case the aqueous liquid is water, supplying both the solution and a stream of the alcohol to the crystallisation vessel;

(b) passing vapour phase of the mixture through a sorption zone containing a water vapour sorbent to selectively adsorb water from the vapour phase to obtain a vapour phase depleted in water and enriched in the solvent and water-saturated water vapour sorbent;

(c) enriching the mixture in the crystallisation vessel in solvent by (i) recycling at least part of the vapour phase depleted in water and enriched in the solvent to the crystallisation vessel or (ii) withdrawing vapour phase depleted in water from the process and adding solvent from an external source to the crystallisation vessel;

(d) allowing solid crystals of the sucrose to precipitate from the solution in the crystallisation vessel at a crystallisation temperature; and (e) discharging precipitated solid crystals of the sucrose from the crystallisation vessel and discharging a solution of non-crystallised sucrose in water-solvent mixture from the crystallisation vessel.

7. The process according to claim 6, wherein the alcohol is ethanol or 1-butanol, and the process further comprises:

(f) fermenting at least part of the remaining sucrose in the solid extracted biomass and/or of the non-crystallised sucrose discharged from the crystallisation vessel in step (e) into the alcohol to obtain a fermentation broth comprising the alcohol;

(g) separating at least part of the alcohol obtained in fermentation step (f) from the broth to obtain alcohol product.

8. The process according to claim 7, further comprising:

(h) recycling part of the alcohol produced in step (f) to extraction step (a1) and/or to the crystallisation vessel.

9. The process according to claim 6, further comprising:

(i) anaerobically fermenting the fermentation broth from which the alcohol has been separated in step (g) and/or the solid extracted biomass, optionally together with leaves and small particles of the sucrose-containing biomass, to obtain biogas;

(j) fuelling an engine with the biogas to produce energy and heat.

10. The process according to claim 9, further comprising:

(k) desorbing water from the saturated water vapour sorbent obtained in step (b) by heating the saturated water vapour sorbent using the heat produced in step (j) to obtain regenerated water vapour sorbent and steam.

11. The process according to claim 10, further comprising:

(l) using the steam obtained in step (k) to (i) separate at least part of the alcohol from the fermentation broth in step (g) by stripping or distillation and/or to (ii) heat the crystallisation vessel to the crystallisation temperature.

12. The process according to claim 1, wherein the water vapour sorbent is a molecular sieve.

13. The process according to claim 12, wherein the molecular sieve comprises pores with a minimum diameter of 3.0 Å.

14. The process according to claim 1, wherein the crystallisation temperature is from 60 to 90° C.

15. The process according to claim 1, wherein step (b) comprises pumping the vapour phase of the mixture to the sorption zone.

16. The process according to claim 1, wherein step (c) comprises discharging at least part of the vapour phase depleted in water and enriched in the solvent from the sorption zone and recycling the discharged vapour phase to the crystallisation vessel.

17. A process for crystallisation of a water-soluble compound from a solution, comprising:

(a) providing, in a crystallisation vessel, a solution of the water-soluble compound in a mixture of water and a solvent, wherein the water-soluble compound has a lower solubility in the solvent than in water;

(b) passing vapour phase of the mixture through a sorption zone containing a water vapour sorbent to selectively adsorb water from the vapour phase to obtain a vapour phase depleted in water and enriched in the solvent and water-saturated water vapour sorbent;

(c) enriching the mixture in the crystallisation vessel in solvent by (i) recycling at least part of the vapour phase depleted in water and enriched in the solvent to the crystallisation vessel or (ii) withdrawing vapour phase depleted in water from the process and adding solvent from an external source to the crystallisation vessel;

(d) allowing solid crystals of the water-soluble compound to precipitate from the solution in the crystallisation vessel at a crystallisation temperature of 60 to 90° C.; and (e) discharging precipitated solid crystals of the water-soluble compound from the crystallisation vessel and discharging a solution of non-crystallised water-soluble compound in water-solvent mixture from the crystallisation vessel.

18. The process according to claim 17, wherein the water-soluble compound is a saccharide with one to five monose units.

19. The process according to claim 18, wherein the water-soluble compound is sucrose.

20. The process according to claim 17, wherein the solvent is an alcohol with one to four carbon atoms or a mixture of two or more thereof.

21. The process according to claim 17, wherein the solvent is ethanol or 1-butanol.

22. The process according to claim 21, wherein the solvent is ethanol.

23. The process according to claim 19, wherein the sucrose is supplied to the crystallization vessel by diluting sugar palm juice with the alcohol or with water and the alcohol.

24. The process according to claim 17, wherein the water vapour sorbent is a molecular sieve.

25. The process according to claim 24, wherein the molecular sieve comprises pores with a minimum diameter of 3.0 Å.

26. The process according to claim 17, wherein step (b) comprises pumping the vapour phase of the mixture to the sorption zone.

27. The process according to claim 17, wherein step (c) comprises discharging at least part of the vapour phase depleted in water and enriched in the solvent from the sorption zone and recycling the discharged vapour phase to the crystallisation vessel.

* * * * *